United States Patent
Chess

[11] Patent Number: 5,282,797
[45] Date of Patent: Feb. 1, 1994

[54] METHOD FOR TREATING CUTANEOUS VASCULAR LESIONS

[76] Inventor: Cyrus Chess, 49 Blue Spruce Cir., Weston, Conn. 06883

[21] Appl. No.: 706,243

[22] Filed: May 28, 1991

Related U.S. Application Data

[63] Continuation-in-part of Ser. No. 358,890, May 30, 1989, Pat. No. 5,057,104.

[51] Int. Cl.$^5$ .............................................. A61N 5/06
[52] U.S. Cl. .......................................... 606/9; 606/13; 606/27; 606/31; 607/89; 607/104
[58] Field of Search ..................... 128/898, 395–399, 128/403; 606/9, 20, 24–26, 28–31

[56] References Cited

U.S. PATENT DOCUMENTS

| | | | |
|---|---|---|---|
| 3,307,553 | 3/1967 | Liebener | 128/400 |
| 3,821,510 | 6/1974 | Muncheryan | 606/16 |
| 3,967,627 | 7/1976 | Brown | 128/400 |
| 4,122,853 | 2/1979 | Smith | 606/6 |
| 4,140,130 | 10/1978 | Storm, III | 128/400 |
| 4,381,007 | 4/1983 | Doss | 606/5 |
| 4,559,942 | 12/1988 | Eisenberg | 606/6 |
| 4,608,979 | 9/1986 | Breidenthal et al. | 606/127 |

FOREIGN PATENT DOCUMENTS

| | | | |
|---|---|---|---|
| 073617 | 3/1983 | European Pat. Off. | |
| 166123 | 12/1981 | Japan | 606/9 |

OTHER PUBLICATIONS

*Plasti. Reconstr. Surg.* 6902:78 (1982), article entitled "Chilling Port Wine Stains Improves The Response to Argon Laser TherapyP" By B. A. Gilchrest, S. Rosen and J. M. Noe.

*Plasti. Reconstr. Surg.* 75.1:42–45 (1985), article entitled "The Benefit of Chilling In Argon-Laser Treatment Of Port-Wine Stains" by B. Dreno, T. Patrice, P. Litoux and H. Barriere.

*Primary Examiner*—David M. Shay
*Attorney, Agent, or Firm*—Ohlandt, Greeley & Ruggiero

[57] ABSTRACT

A method is provided of treating cutaneous vascular lesions in a target area of a patient. The method comprises the steps of passing a laser beam against and through a cooling medium, and then passing the laser beam against and through a patient's epidermis to the target area while simultaneously subjecting the patient's epidermis to a cooling medium at the location of the epidermis entered by the laser beam. An apparatus for treating a cutaneous vascular lesion in a target area of a patient comprises a laser beam source for directing a laser beam against and through a predetermined location of an epidermis of the patient to the target area and a flexible bag for containing a cooling medium and for subjecting the patient's epidermis to the cooling medium at the target area simultaneous with the application of the laser beam thereto. The flexible bag is positioned between the laser beam source and the target area of the patient's epidermis.

7 Claims, 3 Drawing Sheets

METHOD FOR TREATING CUTANEOUS VASCULAR LESIONS

RELATED APPLICATION

This application is a continuation-in-part of application Ser. No. 07/358,890, filed May 30, 1989, now U.S. Pat. No. 5,057,104 issued Oct. 15, 1991.

BACKGROUND OF THE INVENTION

I. Field of the Invention

The present invention relates generally to a method and apparatus for treating cutaneous vascular lesions and, more particularly, to such a method and apparatus in which the cutaneous vascular lesions are treated by simultaneously cooling the site of the lesions while delivering laser light to the site.

II. Description of the Prior Art

A cutaneous vascular lesions, such as telangiectasia or spider capillaries of the lower extremities, is a condition where previously microscopic blood vessels have become dilated. They are visible through the skin appearing as red, blue or purple variably tortuous lines or patches. The causes of this abnormal enlargement of vessels are not fully understood, and although they are of little medical consequence their cosmetic significance can be great. This is a widespread problem that may cause much concern for those afflicted.

Sclerotherapy is the treatment that is now used. It is considered to be safe, appropriate and relatively effective. Sclerotherapy entails the intravascular injection of one of a variety of agents into the abnormal blood vessels. The substance injected injures the inside of the capillary causing it to shrink or disappear. This treatment is variably painful, approximately seventy percent (70%) effective and usually requires one to two months waiting before improvement can be seen. There can occur, unpredictably, echymotic or hyperpigmented marks as a side effect and these marks may take many months to fade. Scabbing of injection sites, perhaps due to extravasation of the injected sclerosing agent, may also occur.

Laser surgery with a variety of different lasers (CO2, Argon, tunable dye) has been utilized in an attempt to find a less painful, more effective treatment. The desire to avoid side effects has also prompted a search for alternative treatment. To date, the ability to improve the outcome by virtue of laser surgery has, unfortunately, not been possible for reasons explained below.

The disadvantages of sclerotherapy, as described above, include the pain of treatment, only partial improvement, and the possibility of long term discoloration that can be more noticeable than the telangiectasia. Although laser surgery (Argon or tunable dye) hurts less than sclerotherapy, it has not offered an improved result. Due to the interaction between laser light and melanin pigments in the epidermis that overlies the target vessels, there can be long term hyperpigmentation, persistent scabs and sometimes permanent scarring.

U.S. Pat. No. 4,122,853 to Smith, which issued on Oct. 31, 1978, provides an infrared laser photocautery device. There is provided means for delivering a liquid through a passageway for irrigating the area being treated. The fluid is not used for cooling, and the utility of the device is primarily for photo-cauterizing intraocular muscular tissue.

U.S. Pat. No. 4,381,007 to Doss, which issued on Apr. 26, 1983, relates to a multipolar probe apparatus using radio frequency energy to reshape the cornea of an eye. The surface of the cornea is flushed continuously with an electrically conductive liquid coolant during the operation. No lasers are involved, and the use of the apparatus is limited to reshaping corneas.

U.S. Pat. No. 4,559,942 to Eisenberg, which issued on Dec. 24, 1985, is a method of using a laser for cataract surgery. The laser passes through a probe to the target tissue and an air cushion is maintained between the probe and the target tissue to prevent physical contact between the radiation outlet of the probe and the target tissue during laser irradiation. At column 4, lines 39–41, it is emphasized that due to air cushion between the probe and the target tissue, the laser radiation passes to the tissue with little loss of heat, thus indicating that it is Eisenberg's intent to conserve, not to dissipate, heat.

U.S. Pat. No. 4,608,979 to Breidenthal, et al, which issued on Sep. 2, 1986, is directed to nonsurgically fragmenting of kidney stones by an apparatus which produces focused shock waves. A truncated ellipsoidal reflector is positioned against the patient with one focus coincident with the stone. The reflector is filled with a liquid medium having an acoustical impedance similar to living tissue. A laser beam is focused at the remaining focus, thereby producing a shock wave which is coupled through the liquid medium and the patients tissue and focused at the stone, to impart a fragmenting stress to the stone. The liquid medium is not used for cooling purposes.

European Patent application No. 073,617 to Pemberg, which has a priority dated of Aug. 25, 1981, provides a laser dental hard piece with a water/air supply tube. There is provided means for pulsating the water alternately with the laser beam if the laser beam will not function efficiently in a water-vapor atmosphere. There is no mention of using water or air for cooling.

In *Plasti. Reconstr. Surg.* 6902:78 (1982) in an article titled "Chilling Port Wine Stains Improves The Response To Argon Laser Therapy" by B. A. Gilchrest, S. Rosen and J. M. Noe, the data obtained in this study suggests the potential benefit of port wine lesional modification by chilling the lesional sites by applying ice thereto for 2 to 3 minutes and then subjecting the sites to Argon laser therapy. It is further suggested that the benefit is due to reduced heat injury of nonvascular elements in the skin.

In *Plasti. Reconstr. Surg.* 75.1:42–45 (1985) in an article titled "The Benefit Of Chilling In Argon-Laser Treatment Of Port-Wine Stains" by B. Dreno, T. Patrice, P. Litoux and H. Barriere, the authors compare results obtained in Argon laser treatment of port-wine stains with and without preliminary chilling, noting that the success rate is considerably greater with the former procedure (68.6 percent) then with the latter (37.5 percent). The patients were classified as having good or unsatisfactory results four months after treatment. A good result corresponded to an evident blanching of the treated area, and an unsatisfactory result corresponded to slight or no blanching of the treated area.

It should be noted that in the latter two studies, Argon laser treatment and cooling did not occur simultaneously.

The following patents were cited during the prosecution of the parent to this continuation-in-part application. U.S. Pat. No. 3,821,510 to Muncheryan, which issued on Jun. 28, 1974, is directed to a hand-held laser beam transmitting and focusing device in which there is provided means for selectively passing therethrough one or more fluids simultaneously with the operation of the device.

U.S. Pat. No. 3,307,553 to Liebener, which issued on Mar. 7, 1967, is directed to an apparatus for cooling irradiated skin areas. It provides a container having a parallel faces that are perpendicular to the treatment beam, but uses cooling medium flowing therethrough, not a stationary container, for cooling of the skin areas.

U.S. Pat. No. 3,967,627 to Brown, which issued on Jul. 6, 1976, is directed to hot/cold applicator system that provides for the use of a heat exchanger and re-circulation of recooled liquid.

U.S. Pat. No. 4,140,130 to Storm III, which issued on Feb. 20, 1979, is directed to an electrode structure for emitting electromagnetic radiation.

These patents neither provides a transparent container or medium nor the positioning of the cooling medium between the laser beam source and the target area as provided for the present application.

SUMMARY OF THE INVENTION

Against the foregoing background, it is a primary object of the present invention to provide a substantially improved method for treating cutaneous vascular lesions, particularly lower extremity telangiectasia.

It is another important object of the present invention to provide substantially improved apparatus for treating cutaneous vascular lesions, particularly lower extremity telangiectasia.

It is still another important object of the present invention to provide such an improved method and apparatus for allowing for laser photo-coagulation and destruction of lower extremity telangiectasia while protecting the epidermal compartment from thermal injury that otherwise results from melanin absorption of laser light by cooling the epidermis and while simultaneously passing laser light through the cooled epidermis to the target vessels in the dermis.

It is yet another important object of the present invention to provide such an improved method and apparatus that minimize injury to normal skin structures to reduce resulting pain and side effects of scabbing, scarring and/or hyperpigmentation.

It is a still further important object of the present invention to provide such an improved method and apparatus that utilize laser treatment and avoids any refraction or other alteration of the physical characteristics of the laser light.

It is yet a further important object of the present invention to provide such an improved method and apparatus that provides a cooling medium that can conform to the target area.

To the accomplishment of the foregoing objects and advantages, the method of the present invention, in brief summary, comprises the steps of passing a laser beam against and through a cooling medium, and then passing the laser beam against and through a patient's epidermis to the target area while simultaneously subjecting the patient's epidermis to a cooling medium at the location of the epidermis entered by the laser beam.

The apparatus of the present invention, in brief summary, comprises a laser beam source for directing a laser beam against and through a predetermined location of an epidermis of the patient to the target area and a flexible bag for containing a cooling medium and for subjecting the patient's epidermis to the cooling medium at the target area simultaneous with the application of the laser beam thereto. The flexible bag is positioned between the laser beam source and the target area of the patient's epidermis.

BRIEF DESCRIPTION OF THE DRAWINGS

The foregoing and still other objects and advantages of the present invention will be more apparent from the following detailed explanation of the preferred embodiments of the invention in connection with the accompanying drawings wherein.

DESCRIPTION OF THE PREFERRED EMBODIMENTS

The purpose of the present invention is to provide a new laser surgery method and apparatus to allow for laser photo-coagulation and destruction of cutaneous vascular lesions, such as, for example, lower extremity telangiectasia. Simultaneously, the epidermal compartment of the patient is protected from thermal injury that otherwise would result from melanin absorption of laser energy. Since laser light must pass through the melanin containing epidermis, on its way to the target vessels in the dermis, it is not possible to prevent some degree of heat generation when laser light hits melanin pigment. Indeed, yellow (tunable dye) laser light, although less efficiently absorbed by melanin than is blue-green (Argon) laser light, still causes significant hyperpigmentation as a long term side effect. In the present invention, the epidermis is cooled simultaneously with the use of laser light. This cooling dissipates the heat generated by absorption of that light by melanin, thereby minimizing injury to normal skin structures to reduce resulting pain and side effects of scabbing, scarring and/or hyperpigmentation. The simultaneous cooling and lasering of the target area is achieved by one or more of the following embodiments of the present apparatus.

Figure 1:
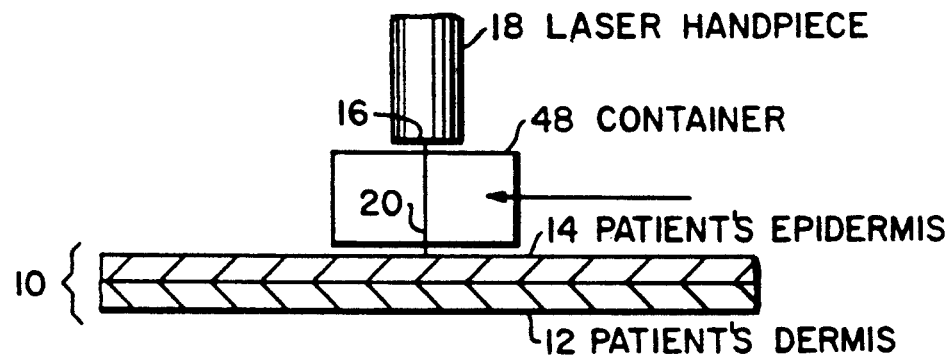
FIG. 1 is a somewhat schematic view showing a first preferred form of the apparatus embodying the present invention being used to perform the method of the invention.
Figure 2:
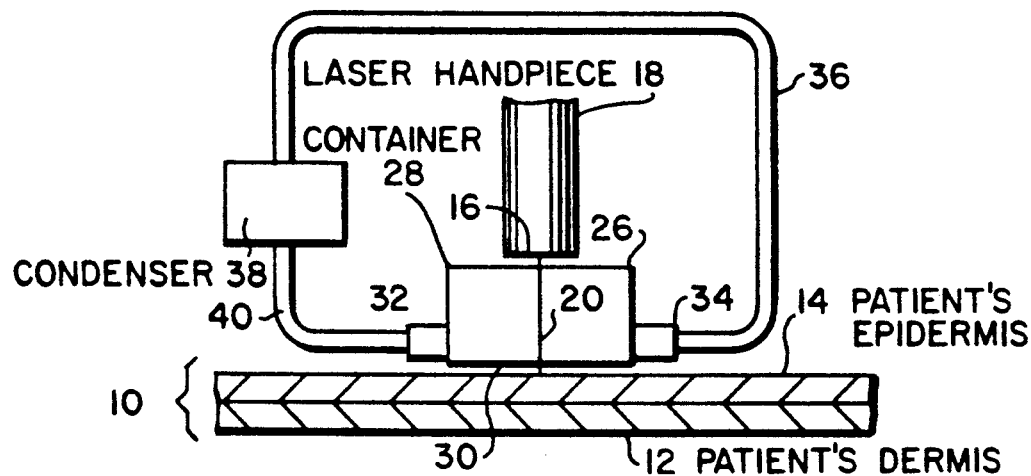
FIG. 2 is a view, similar to FIG. 1, showing a second preferred form of the apparatus embodying the present invention being used to perform the method of the invention.
Figure 3:
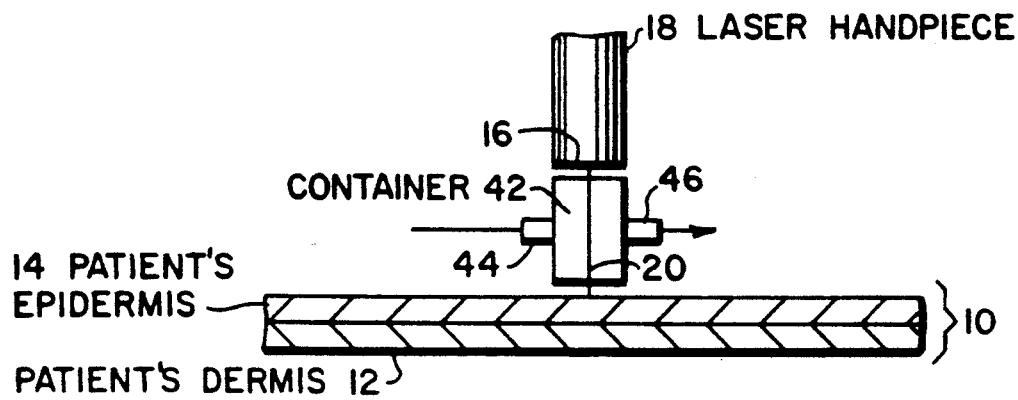
FIG. 3 is a view, similar to FIG. 1, showing a third preferred form of the apparatus embodying the present invention being used to perform the method of the invention.

Referring to the figures and, in particular, FIGS. 1, 2 and 3, there is shown three embodiments of the apparatus 1 for performing the method of the present invention. In each figure, the apparatus 1 is illustrated in the course of treating a cutaneous vascular lesion indicated as a target area 10 in a patient's dermis 12 that is overlaid by the patient's epidermis 14. While the target area 10 is, preferably, located in a lower extremity of the patient, it is possible to practice the teachings of the present invention on other areas of the patient's body.

FIGS. 1, 2 and 3 each depicts an embodiment of the apparatus 1 of the present invention. Each apparatus 1 includes a laser beam source 16 and means for subjecting the target area 10 to a cooling means. The laser beam source 16, that may or may not be housed in a laser handpiece 18, has a laser beam 20 that is shown emanating therefrom. The laser beam source 16 is directed at the target area 10 so that the laser beam 20 impinges on a predetermined location or target area of the epidermis 14. In a preferred embodiment, the laser beam source 16 is substantially at right angles to the target area 10. The epidermis 14 contains melanin which would absorb laser energy, with resultant thermal injury, as discussed above. In a preferred embodiment, the laser beam 20 is an Argon laser beam.

The apparatus of FIG. 1 includes a transparent container 48 has a cooling means or medium that preferably is a cooling fluid. The cooling fluid is a suitable liquid such as ice water. There are no inlet and outlet tubes. Accordingly, the ice water is substantially non-flowing. Container 48 is a first container and is replaceable by a second container (also 48) that contains more cooling fluid when the fluid or liquid in first container 48 becomes too warm for efficient use. The then warmed cooling fluid in the first container 48 can then be re-cooled so as to be ready for reuse.

As shown in FIG. 1, the container 48 for the cooling medium is positioned between the target area 10 and the laser beam source 16. Accordingly, the laser beam 20 emanating from the laser beam source 16 passes from the laser beam source through the cooling medium to the target area 10. Therefore, the target area 10 is cooled by the cooling medium in the container 48 and is treated by the laser beam 20 at the same time.

In the apparatus of FIG. 2, the cooling means is, preferably, a cooling fluid provided in a transparent container 26 having a pair of parallel opposite faces 28 and 30. The cooling fluid is applied at the treatment site or target area 10 simultaneous with the application of the laser beam 20. The laser beam 20 is, preferably, substantially perpendicular to the parallel opposite faces. Container 26 has an inlet tube 32 for inserting refrigerated cooling fluid into the container and an outlet tube 34 for removing heated fluid from the container in order to provide a stream of refrigerated cooling fluid in a direction parallel to and adjacent the outer surface of epidermis 14. Suitable piping 36 is provided to return the now heated fluid from outlet tube 34 through a condenser 38 to cool the fluid. Suitable piping 40 is also provided for returning fluid (now again refrigerated) to inlet tube 32 and then once again into container 26.

Thus, the apparatus of FIG. 2 also includes means for re-cooling heated fluid and thereafter re-introducing the re-cooled fluid into inlet tube 32.

The apparatus of FIG. 3 has a transparent container 42 with an inlet tube 44 and an outlet tube 46 for re-cycling cooling medium. The cooling medium maybe a liquid or a gas. It is preferred that the cooling medium be a non-flammable transparent liquid. The outlet tube 46 may be connected to a waste line (not shown) or connected back to inlet tube 44 via piping and a condenser as in the apparatus of FIG. 2. The apparatus of FIG. 3 illustrates that the container 42 is not attached to the laser handpiece 18 at the laser beam source 16. The container may, however, be attached to the laser handpiece at the laser beam source.

Figure 4:
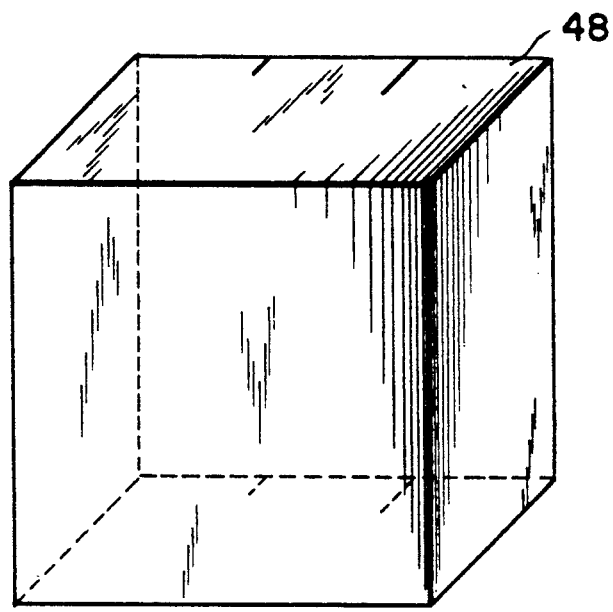
FIG. 4 is an enlarged perspective view showing a coolant container that is a component of the apparatus of FIG. 3.

FIG. 4 is an enlarged perspective view of container 48 of FIG. 1. As shown in FIG. 4, container 48 is a rectangular, parallel pipe structure which is about 6 inches (15.2 cm) by 6 inches (15.2 cm) by 2 inches (5.1 cm). The container 48 maybe fabricated of glass panels 0.125 inches (0.3 cm) thick.

Figure 5:
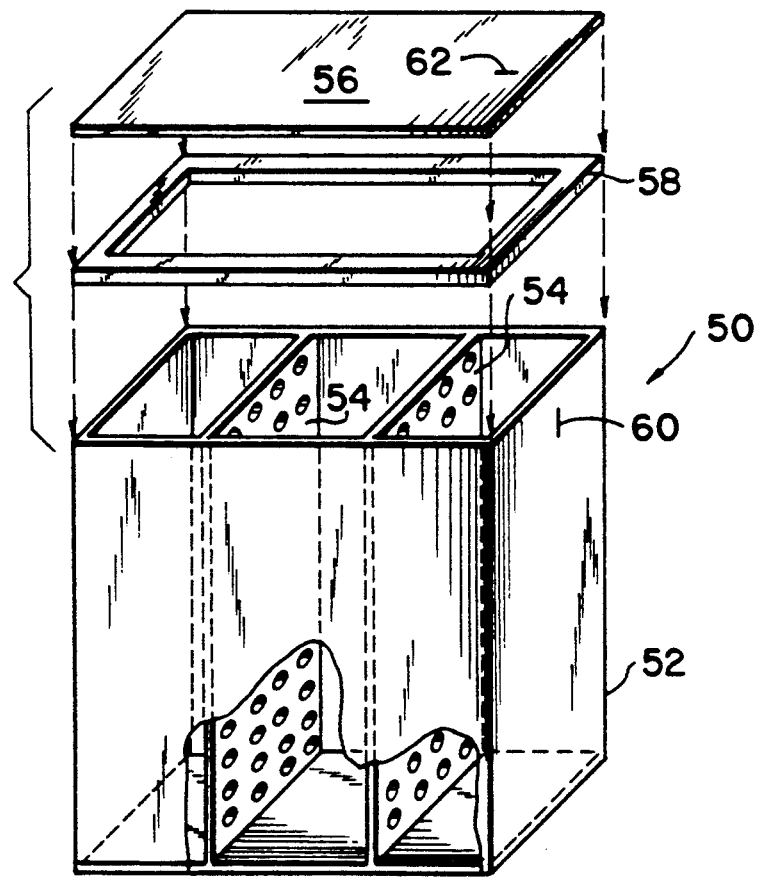
FIG. 5 is an enlarged perspective view similar to FIG. 4 but showing a modified form of a coolant container that may be used instead of the container of FIG. 4.

FIG. 5 is perspective view of a container 50 that is a modified form of a container (instead of container 48) for use in the apparatus of FIG. 1. The container 50 has a body 52 for containing the cooling fluid. The body 52 has perforated, spaced, parallel internal walls 54, a top 56 that covers body 52, and a sealing element 58 interposed between the body and the top. Sealing element 58 may be silicone. body 52 is attached at 60 and top 56 is attached at 62.

The body 52 and the top 56 may be fabricate of glass panels 0.125 inches (0.3 cm) thick. The dimension of body 52 may be about 6 inches (15.2 cm) wide by 1 inch (2.5 cm) deep by 7 inches (17.8 cm) high. Thus, the top 56 is about 6 inches (15.2 cm) by 1 inch (2.5 cm).

The following is the result of the application of an Argon laser treatment of lower extremity telangiectasia achieved with the simultaneous cooling of the treatment site. Specifically, pulses of two tenths of a second were applied onto three areas of a thigh of a subject. Each area was treated for approximately 15 minutes.

| Results Of Argon Laser Treatment Of Lower Extremity Telangiectasia Achieved With Simultaneous Cooling Of The Treatment Site. | | | | |
|---|---|---|---|---|
| SUBJECTIVE | | OBJECTIVE | | |
| Pain of Treatment | Pain After Treatment | Immediate Response to Treatment (Nature of Wound) | Time To Full Healing | Result (1 month After Treatment) |
| Moderate and less painful than injection sclerotherapy | None | No scab Erythema and urtication of skin overlying treated vessels No echymosis or bleeding | 2-4 wks | Of the three sites which were fully treated: one is Excellent (98% gone) one is Good (70%-80% gone) one is Poor (20%-30% Gone) No scaring at any site |

Final result judged at four months—all three sites good to perfect. All three sites are without scarring, and treated vessels are gone or markedly reduced in appearance.

These results prove that the epidermis can be at least partly protected from thermal injury by virtue of simultaneous lasing and cooling. Without cooling, the same manner of laser usage routinely causes prominent scabs that persist for 3-6 weeks. Further, there are red to purple colored scars that require 4-12 months to fade. Simultaneous cooling has allowed for a virtual absence of scabbing and rapid resolution of the wound, without persistent marking or scaring.

It is likely that the use of other kinds of lasers (tunable dye) with simultaneous cooling will allow for more consistent results, with at least equally rapid healing and resolution, and less, if any, discomfort.

Figure 6:
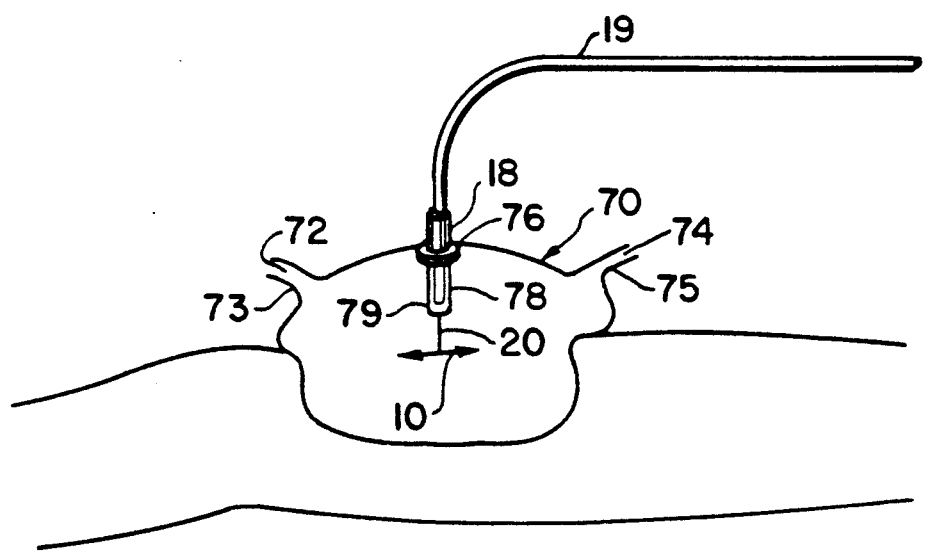
FIG. 6 is a view showing a fourth preferred form of the apparatus embodying the present invention being used to perform the method of the invention.

FIG. 6 is another embodiment of the present invention. It has now been found that the cooling medium can be maintained in a flexible container or bag 70. The flexible container 70 is adapted to fit the contour of the patient's target area. For example, the target area 10, as shown in FIG. 6, can be the knee and thigh area of a patient's leg. Accordingly, the flexible bag 70 when applied to the target area 10 eliminates any space that may otherwise exist between the cooling medium container and the target area. The elimination of the space between the container and the target area was attempted by the container provided for in the parent to this continuation-in-part application. In this application, the container or bag can adapt to the contour of the target area so as to avoid any space or any portion of the target area. The apparatus of this embodiment includes the flexible container or bag 70 and a cooling medium, such as gas or water, therein. In the preferred embodiment, the cooling medium is a refrigerated fluid, such as refrigerated or ice water.

In a preferred embodiment, the flexible bag 70 has an inlet opening 72, an outlet opening 74, an aperture 76 with a sleeve 78 for invagination of the laser handpiece 18. The inlet opening 72, that can be an inlet tube 73, permits the cooling medium to enter into the flexible bag 70, while the outlet opening 74, that can also be an outlet tube 75, permits the warmed cooling fluid to be removed from the flexible bag. Accordingly, the warmed cooling medium can be taken to a cooling mechanism that is external to the flexible bag 70, and the re-cooled medium can be reintroduced by inlet opening 72 into the flexible bag. In a more preferred embodiment, the inlet opening 72 and the outlet opening 74 are integrally portions of the flexible bag 70. In addition, the inlet and outlet openings 72, 74, respectively, are formed in the shape of a tube to facilitate the insertion of new or re-cooled cooling medium and the exit of the warmed cooling medium from the flexible bag 70.

The aperture 76 and the sleeve 78 are sized to invaginate the laser handpiece 18. The aperture 76 should be positioned at the top of the flexible bag 70. The sleeve 78, that is sized to hold a principle portion of the laser handpiece 18, permits the laser beam 20 to pierce the end 79 of the sleeve and, thereby, contact the target area 10. By the construction of the sleeve 78, the laser handpiece 18 can, except for the materials of the flexible bag, practically contact the target area 10. Therefore, there may not be any cooling medium between the end 79 of the sleeve 78 and the target area 10 or, alternatively, the amount of the cooling medium therebetween would be minimal. The cooling medium does not effect the direction or placement of the laser beam 20.

The flexible bag 70 is, preferably, made of a material that is transparent to a laser beam or laser light. The transparency of this material is such that it allows one to observe the target area or skin of the patient that has the flexible bag 70 thereon. Likewise, the sleeve 78 is made of the same transparent material. In a preferred embodiment, the sleeve is an integral part of the flexible bag 70.

The entire flexible bag 70, including the aperture 76 and the sleeve 78, is watertight, except that the inlet and outlet openings 72, 74, respectively, permit water or the cooling medium to pass therethrough.

As shown in FIG. 6, the laser handpiece 18 may be connected to or at the end of fiber optic tubing 19. This facilitates insertion of the laser handpiece 18 in the sleeve 78.

The invention having been thus described with particular reference to the preferred forms thereof, it will be obvious that various changes and modifications may be made therein without departing from the spirit and scope of the invention as defined in the appended claims.

Wherefore, I claim:

1. A method of treating cutaneous vascular lesions in a target area of a patient, said method comprising the steps of:

positioning a cooling medium contained in a closed container having a pair of walls adjacent a location of an epidermis of the patient, and positioning a laser beam adjacent the container;

passing the laser beam through one of the pair of walls of the container and then through the cooling medium contained in the container;

then passing the laser beam through the other of the pair of walls of the container; and thereafter passing the laser beam through the location of the epidermis of the patient to the target area while simultaneously subjecting the location of the epidermis to the cooling medium.

2. The method according to claim 1, wherein the laser beam is directed against the epidermis substantially at right angles to the location of the epidermis.

3. The method according to claim 1, further comprising the step of removing the cooling medium when the cooling medium is too warm to cool the epidermis and replacing the cooling medium with new cooling medium.

4. The method according to claim 1, wherein said cooling medium is a fluid or a gas.

5. The method according to claim 4, wherein said fluid or gas is transparent.

6. A method according to claim 4, wherein the fluid is a non-moving transparent liquid.

7. A method according to claim 6, wherein the transparent liquid is ice water.

* * * * *